(12) United States Patent
Brown et al.

(10) Patent No.: US 6,603,924 B2
(45) Date of Patent: Aug. 5, 2003

(54) THERMAL VAPORIZER, CONTAINER FOR THE THERMAL VAPORIZER AND A THERMAL VAPORIZER ASSEMBLY

(75) Inventors: Colin William Brown, Surrey (GB); Gerald Leslie Hart, deceased, late of Surrey (GB), Legal heir, Susan Hart; Guy Edward Naish, Oxfordshire (GB); Kishen Gohil, Surrey (GB); Mónica Mascato Dominguez, Vigo-Pontevedra (ES)

(73) Assignee: Zelnova, S.A. (ES)

( * ) Notice: Subject to any disclaimer, the term of this patent is extended or adjusted under 35 U.S.C. 154(b) by 0 days.

(21) Appl. No.: 10/119,419

(22) Filed: Apr. 9, 2002

(65) Prior Publication Data

US 2002/0181946 A1 Dec. 5, 2002

(30) Foreign Application Priority Data

Apr. 9, 2001 (EP) ............................. 01108825

(51) Int. Cl.[7] .............................. F24F 6/08; H05B 3/08
(52) U.S. Cl. ...................... 392/390; 392/395; 219/541
(58) Field of Search ................... 392/386, 390, 392/392, 394, 395; 219/435, 436, 541, 509, 516, 518

(56) References Cited

U.S. PATENT DOCUMENTS

| | | | |
|---|---|---|---|
| 2,269,689 A | * | 1/1942 | Reichold ................... 219/435 |
| 4,095,090 A | * | 6/1978 | Pianezza ................... 219/441 |
| 4,467,177 A | | 8/1984 | Zobele |
| 4,588,874 A | | 5/1986 | Napierski |
| 5,038,394 A | * | 8/1991 | Hasegawa et al. .......... 392/395 |
| 5,095,647 A | | 3/1992 | Zobele et al. |
| 5,290,546 A | | 3/1994 | Hasegawa et al. |
| 5,647,053 A | | 7/1997 | Schroeder et al. |
| 6,072,161 A | * | 6/2000 | Stein ........................ 219/432 |
| 6,278,840 B1 | * | 8/2001 | Basaganas Millan ....... 392/390 |

FOREIGN PATENT DOCUMENTS

| | | |
|---|---|---|
| DE | 3345134 | 6/1985 |
| DE | 3701499 | 7/1988 |
| EP | 0962132 | 8/1999 |

* cited by examiner

Primary Examiner—Sang Paik
(74) Attorney, Agent, or Firm—Ostrolenk, Faber, Gerb & Soffen, LLP

(57) ABSTRACT

A thermal vaporizer for a liquid formulation comprising a volatile active, a container for said vaporizer and a thermal vaporizer assembly. The vaporizer (A) comprises a housing (1) having a heater unit (2) for evaporating the liquid formulation, a mounting (8) for a container (50) for the liquid formulation, a passage (5) for a wick means (52) to be heated by the heater unit (2), at least one outlet (6) for evaporated volatile active and an electrical contact connected to said heater unit (2). The vaporizer selectively operates the heater unit at, at least, two different predetermined heating temperatures, such that the heater unit is selectively activated by the container (50).

21 Claims, 7 Drawing Sheets

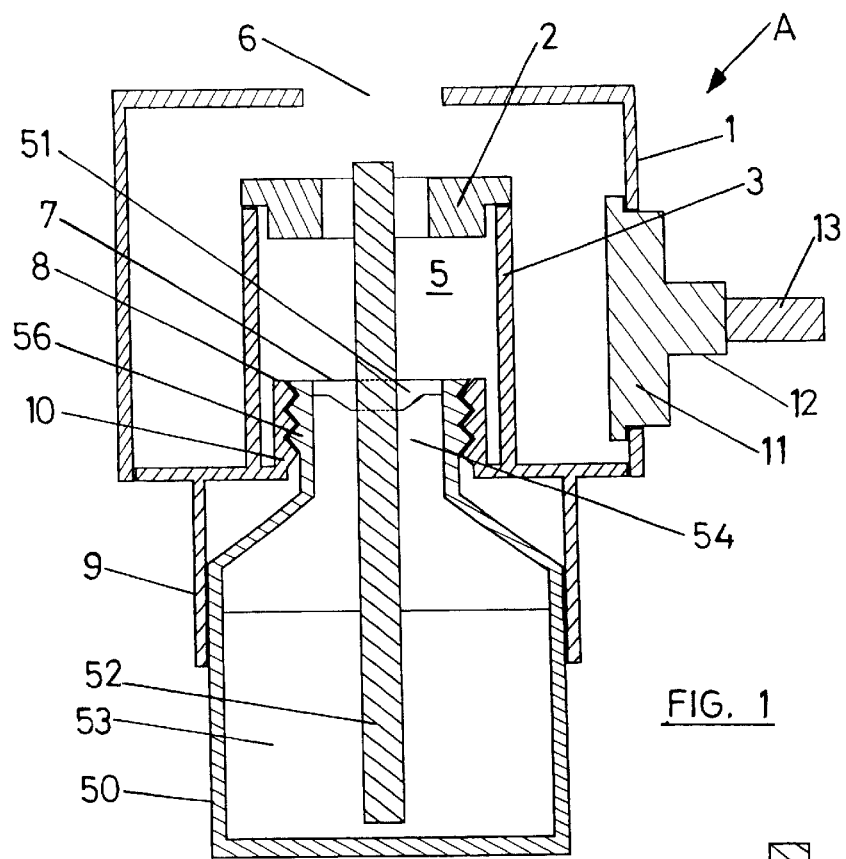
FIG. 1
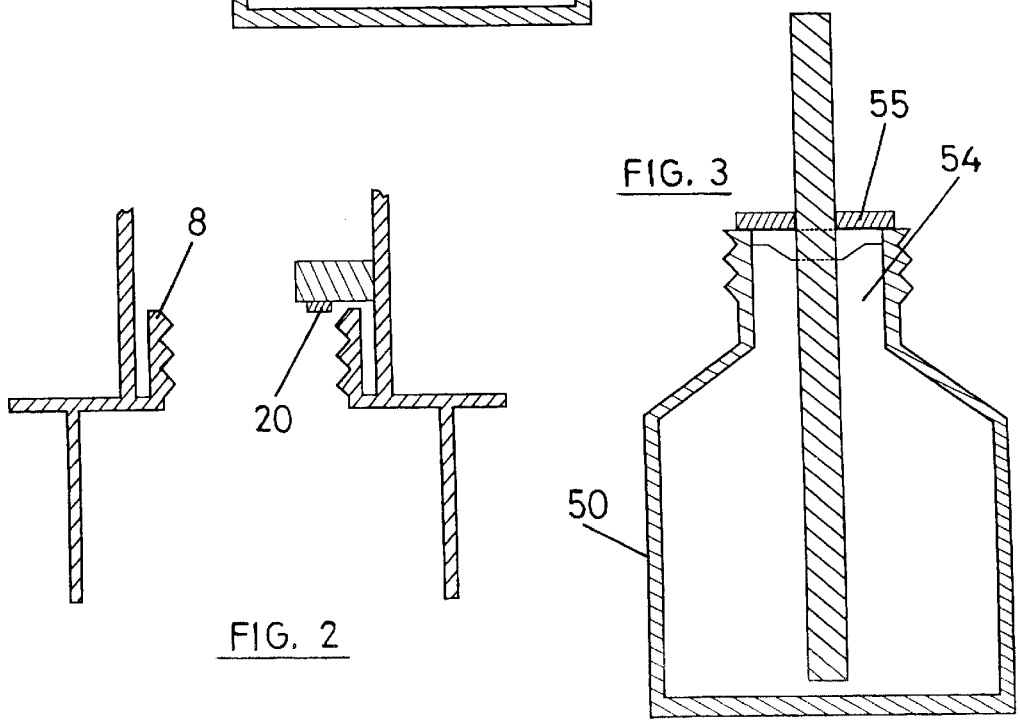
FIG. 2
FIG. 3

THERMAL VAPORIZER, CONTAINER FOR THE THERMAL VAPORIZER AND A THERMAL VAPORIZER ASSEMBLY

TECHNICAL FIELD OF THE INVENTION

The present invention is related to the field of thermal vaporizers for liquid formulations comprising volatile actives.

BACKGROUND OF THE INVENTION

The use of so-called plug-in thermal vaporizers to dispense volatile actives is well known. Some known thermal vaporizers comprise a wick means inserted into a container with a reservoir of liquid volatile active, a heater unit and electric pins which are either fixed, as described in U.S. Pat. No. 4,467,177, or able to be rotated such that the wick can be orientated perpendicular to the ground, as described in U.S. Pat. No. 5,647,053, U.S. Pat. No. 5,290,546, U.S. Pat. No. 5,038,394, U.S. Pat. No. 5,095,647 and EP-A-0 962 132.

In the above-mentioned cases, the vaporizers rely on the air motion resulting from the heat rising from the heater unit and the natural dispersion properties of the volatile liquid to disperse the vapor within a defined area such as a room. The wick means comprises a wick formed in the shape of a rod that draws liquid from a refill container up and into a cylindrical gap formed at the center of a heater coil, through which the wick rod passes. Heat from the coil warms the rod, causing evaporation of the liquid, which is replenished through capillary action up the porous rod. In all cases, the heater unit is arranged to operate at one fixed pre-determined temperature.

There are plug-in units available that are designed to control the evaporation intensity by movement of either the container (such as a refill bottle) and wick in relation to the heater unit, as described in the above-mentioned EP-A-0 962 132 or by moving the heater unit in relation to the wick, as is the case with the commercially available air freshener retailed under the Ambi-Pur brand by Sara Lee. In these cases, the amount of evaporation is controlled by exposing more or less of the wick to the heater unit but the operating temperature of the heater unit is still fixed.

It is common for plug-in liquid vaporizer units to run at two distinct temperatures, depending on the end use of the product. Devices for dispensing an insecticide vapor tend to use ceramic or graphite-based wicks and run at temperatures typically in the region of 110–140 degrees centigrade, as is the case with the Kill-Paff® unit as marketed by Zelnova®. Fragrance dispensing units, such as the Ambi-Pur® brand by Sara Lee®, tend to run at lower temperatures, utilizing cellulose or fiber wicks. As a result of the different wicks and operating temperatures, separate heater units have customarily been specifically designed for each end use.

WO-A-97/39779 discloses a multiple electronic vaporizer for resins, which is provided with a plurality of heated hollow bodies, each hollow body reaching different temperatures according to the type of resin to be evaporated (such as incense, propolis and myrrh).

DE-A-37 01 499 discloses a thermal vaporizer arranged to heat tablets containing active substances. The device is arranged so that two tablets with different active substances (such as one tablet with a fragrance and another tablet with an insecticide) can be heated simultaneously, at different temperatures.

DE-A-33 45 134 and U.S. Pat. No. 4,588,874 also disclose thermal vaporizers for evaporating active substances in tablets. Here, the vaporizers include switches for allowing the vaporizers to be set to operate at different temperatures, n accordance with the active substance to be evaporated. The user is expected to manually operate the respective switch in order to select the correct temperature corresponding to the specific active substance to be evaporated. Of course, this implies a certain risk that the user may forget to set the switch to the correct position, whereby an incorrect heating temperature may be applied to a specific active substance.

In the case of a thermal vaporizer for an active substance housed in a bottle with a wick means, using a too high temperature (for example, for a fragrance dispensing bottle with wick) could cause damage to the wick. On the other hand, using a too low temperature for dispensing an insecticide could result in an ineffective release of the insecticide.

Thus, it would be desirable to reduce the risk for erroneous selection of the operating temperature.

DESCRIPTION OF THE INVENTION

The invention comprises a thermal vaporizer, a container and a thermal vaporizer assembly as defined in the independent claims. Some preferred embodiments of the invention are defined in the dependent claims.

A first aspect of the invention relates to a thermal vaporizer for a liquid formulation comprising a volatile active, said vaporizer comprising a housing having: a heater unit for evaporating the liquid formulation; a mounting for a container for the liquid formulation; a passage for a wick means to be heated by the heater unit; at least one outlet for evaporated volatile active; and an electrical contact connected to said heater unit.

The vaporizer further comprises:
  means for selectively operating the heater unit at, at least, two different predetermined heating temperatures, including selecting means for selecting heating temperature, said selecting means including at least one first selecting means arranged to be selectively activated by the container.

By this way, it is achieved that the container, when applied to the vaporizer (preferably, when mounted in the mounting), may activate the first selecting means. This activation can be achieved by means of providing certain containers with special features or activating means so as to activate the first selecting means when the container is brought into a specific relation with the vaporizer, such as when the container is mounted into the mounting of the vaporizer. Thus, said certain containers (which may be, for example, containers for insecticides) will activate the first selecting means, whereas other containers (which may be, for example, containers for fragrances) will not activate said first selecting means. Thus, the heater unit will only operate at a specific predetermined temperature when a container is applied that has the special activating features or activating means. Examples of such activating means will be discussed in more detail later hereinbelow.

Thus, by means of the invention, it is achieved that the temperature at which the heater unit will operate will be switched over automatically when a specific type of container is applied to the vaporizer, for example, when such a container is mounted into the mounting. That is, the heater unit will be made to operate at a suitable temperature in accordance with the specific type of container used.

Thus, the thermal vaporizer according to the invention can be used for the dispensing of different volatile actives, such as insecticides and fragrances. Depending on the type of fragrance used, the container will or will not be provided with special activating features or activating means, so that the first selecting means will automatically be activated or not activated, in accordance with the specific container (and, thus, volatile active) used. Thus, as long as the correct container is used, there will be no danger (or, at least, a substantially reduced danger) that the heater unit could run at an incorrect temperature for a given volatile active.

The first selecting means can comprise, for example, a displaceable switch element arranged to be displaced by the container when the container is fixed into the mounting.

The first selecting means can also comprise one or more selectively interrupted electric circuits arranged to be closed by a metal (or equivalent) connector on the container when the container is fixed into the mounting. For example, the invention can comprise two incomplete or interrupted circuits whereby at least one of them is completed or closed by a metal connector forming part of the container (for example, of the neck, top or cap of the container) when the container is fixed into the mounting. In that case, the specific design of the metal connector of the container could determine whether a first one, a second one or both of the circuits be completed or closed, thus giving rise the different operating temperatures of the heater unit.

The heater unit can have an annular shape enclosing the passage for the wick means. The wick means can comprise, for example, a ceramic or graphite-based wick, attached to the container so that when the container is fixed into the mounting, the wick will extend through the above-mentioned passage.

The selecting means may further comprise further selecting means, such as a second selecting means for selecting, at least, an off operation mode and an on operation mode. By means of this second selecting means, the vaporizer can be turned off and on. However, in order to operate at a specific predetermined temperature, the vaporizer must not only be turned on but must also be triggered by means of the container activating the first selecting means, as outlined above.

The second selecting means can, for example, be arranged as an on-off switch arranged to be activated by the container when the container is fixed into the mounting (in this way, the heater unit will only be able to operate when a container is mounted in the vaporizer) or as an independent switch means mounted on the housing of the vaporizer and arranged to be operated manually by a user.

The second selecting means and the first selecting means can be arranged so as to make it possible to operate the heater unit at different predetermined temperatures. For example, the heater unit can be arranged to operate at a specific high temperature only when the first selecting means are activated by the container. The heater unit can further be arranged to operate at a low temperature when the second selecting means are in a first on operation mode position and the first selecting means are not activated by the container, at a medium temperature when the second selecting means are in a second on operation mode position and the first selecting means are not activated by the container; and at the specific high temperature only when the first selecting means are activated by the container. In this way, one can achieve that, for example, insecticide may not be released unless the first selecting means are activated by the container but fragrance can be released at two different temperatures (the low one and the medium one mentioned above), as desired by the user who sets the switch of the second selecting means accordingly.

The second selecting means could comprise a rocker switch having, for example, three settings of "off", "low" and "high" and could be used to vary the temperature of the not activated setting of the first selecting means between two pre-set amounts (the above-mentioned low and medium temperatures). Thus, the vaporizer could operate at two levels of fragrance release and one level of insecticide release by the following combinations of the selecting means:

| First selecting means | Second selecting means | Result |
| --- | --- | --- |
| Not activated | Off | No emission |
| Not activated | Low | Low fragrance emission |
| Not activated | High | High fragrance emission |
| Activated | Off | No emission |
| Activated | Low or High | Insecticide emission |

In this case, activating the first selecting means would render the two settings of the second selecting means redundant such that the second selecting means revert to an "on/off" controller. However, it is also possible to utilize the low and high settings of the second selecting means to drive the insecticide emission at two pre-determined levels. Also other alternatives are possible within the scope of the invention. For example, the selecting means could be arranged so that the insecticide emission only takes place when the first selecting means are "activated" and the second selecting means are in a specific position, such as in the "low" position (and no: in the "high" position).

The means for selectively operating the heater unit may include, (at least, a first branch comprising a first resistor and, in series with said resistor, a circuit comprising a diode and a switch coupled in parallel, so that when said switch is in an open position, the supply voltage is applied over the diode and over the first resistor, and when the switch is in a closed position, the supply voltage is fully applied over the first resistor. The switch can be arranged to be in the open position when the first selecting means are not activated by the container and in the closed position when the first selecting means are activated by the container. The means for selectively operating the heater unit may further comprise a second branch comprising a second resistor, said second branch being arranged in parallel with said first branch, whereby said second selecting means are arranged so that depending on the position of said second selecting means, the supply voltage is applied selectively to the first branch or to the second branch so that heating is selectively performed by said first or by said second resistor.

The means for selectively operating the heater unit can also comprise at least one variable resistor, the effective resistance of which depends on a level of activation of the first selecting means.

The heater unit can comprise, for example, a wire-wound resistor or a ceramic block containing an array of discreet resistors or any similar device that generates heat on the application of an electrical supply.

The thermal vaporizer can be for a fragrance or an insecticide or both.

Preferable, the high temperature mentioned above corresponds to a temperature for vaporizing an insecticide, the low temperature corresponds to a temperature for low rate release of fragrance and the medium temperature to a temperature for high rate release of fragrance.

Another aspect of the invention relates to a container for the thermal vaporizer outlined above, whereby said container is provided with activating means for activating the first selecting means of the thermal vaporizer when the container is fixed into the mounting.

The activating means can, for example, be embodied by at least one protruding part of the container. The protruding part can, for example, be a molding.

The protruding part can be arranged at a suitable position of the container, for example, at a mouth portion of the container and/or at a neck or shoulder portion of the container.

The protruding part can form an integral part of the container (for example, in the case of a molded container, the protruding part can be molded integrally with the container). However, the protruding part can also be part of an independent element arranged to be attached to the container; for example, if the container is a bottle, the protruding part could be a collar to be put around the neck of the container, or it could be part of a cap portion of the container, for example, of an insert or cap holding the wick means.

The container can comprise such a closure or cap device including means for holding the wick means firmly in place. Preferably, the closure is not easily removable and cooperates with the wick means in such a way that the wick means is not easily removable from the container.

The container preferably comprises a part which cooperates in a known fashion with the mounting of the thermal vaporizer. For example, the container can be arranged to be fixed into the mounting by screw-thread engagement between an internally threaded portion of the mounting and an externally threaded portion of the container. Of course, also other arrangements for fixing the container into the mounting can be used, such as simple connections based on friction between the container and the mounting, bayonet-type connections, snap-fittings (such that the container is pushed, not screwed, into place), etc.

The protruding part could be, for example, a single, discreet feature or an annular raised portion that runs evenly around a vertical axis of the container (for example, a bottle). An annular feature would be particularly applicable to a screw container where the final orientation of the container may not be controllable. Thus, regardless of the final orientation of the container, the protruding part would still activate the first selecting means. Instead of a complete annular feature (that is, corresponding to an annular protruding portion running all around the container), it could be possible to use, for example, an arcuate protruding part corresponding to a segment of a circle.

For bottles that are snap-fitted or push-fitted (i.e. fitted into the unit in a specific orientation), the protruding part could be a single, discreet device. This would also give the advantage that the first selecting means could be arranged to be only accessible by a small orifice of sufficient size to only let the protruding part of the container in.

As suggested above, the first selecting means can be embodied as a rheostat or similar device, which varies the temperature of the heater unit depending on how far it is engaged. In that case, protruding parts with different dimensions could be provided, in order to displace the first selecting means by predetermined amounts corresponding to predetermined temperatures, depending on the final temperature desired. For example, the higher the protruding part, the higher the temperature at which the heater unit will be made to operate. In that case, the container could, for example, be a standard refill bottle, and collars or caps for said bottle could be provided having protruding parts with different dimensions.

The activating means may also comprise a metal connector or element, arranged so as to close an electrical circuit corresponding to the first selecting means; in that case, said metal connector could be embodied as an integral part of the container or as a separate device, associated with, for example, a collar device or a cap for the container.

Another aspect of the invention relates to a thermal vaporizer assembly comprising a thermal vaporizer and a container as outlined above.

The volatile actives of the thermally vaporizable liquid formulation are preferably selected from the group of fragrances, essential oils, insecticides, bactericides, repellents, drugs, herbicides and fungicides. These volatile actives may be carried by a volatile solvent, for example, water, ethanol, isoparaffin or glycol ethers.

For the purpose of providing a better understanding of the invention, some preferred embodiments of the invention will be described below with reference to the accompanying drawings. However, the scope of the invention should by no means be regarded as restricted to said preferred embodiments.

BRIEF DESCRIPTION OF THE DRAWINGS

FIG. 1 shows a cross-sectional view of the thermal vaporizer.

FIG. 2 shows a cross-sectional view of a special embodiment of the mounting.

FIG. 3 shows a cross-sectional view of a special embodiment of a container in accordance with a preferred embodiment of the invention.

FIGS. 11a & 11b show schematic circuit diagrams corresponding to the electrical circuitry of the heater unit in accordance with another preferred embodiment of the invention.

DESCRIPTION OF SOME PREFERRED EMBODIMENTS OF THE INVENTION

Figure 4A:
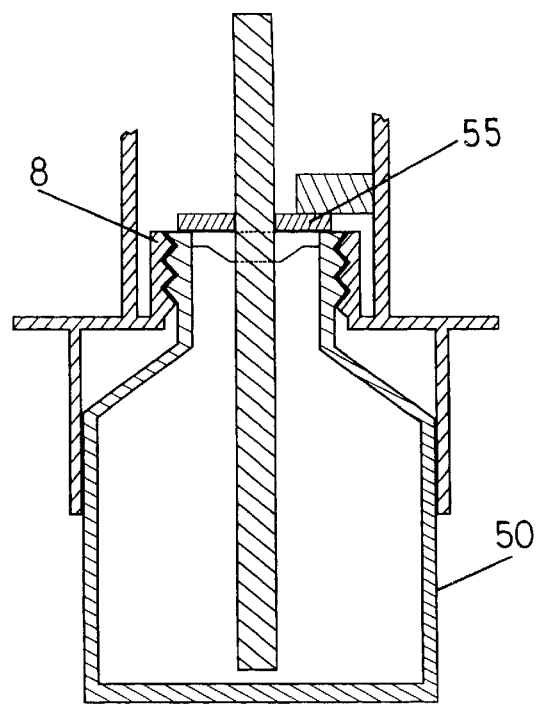
FIGS. 4a & 4b show cross-sectional views of the container within the mounting.

FIG. 1 illustrates a thermal vaporizer A having a housing 1 and, within the housing 1, a heater unit 2, which is preferably annular-shaped. The heater unit 2 is mounted on a support 3 which is fixed at the housing 1. The annular-shaped heater unit 2 and the support 3 form a passage 5 for a wick means 52. The top of the housing 1 has an outlet 6 having the same axis as the passage 5 for the wick means of the heater unit 2. The bottom of the housing has a similar opening 7 having the same axis as the passage 5 of the wick means of the heater unit 2. This opening 7 is surrounded by a mounting 8 which is arranged to firmly hold a container 50. The container 50 is partly covered by a cover 9, which protects the container 50 from impact or damage to be applied or caused thereto from outside. Built into one side of the housing 1 is a circular portion 11 which can rotate about 90 degrees. Inserted into a central extension 12 of this circular portion 11 is an electrical contact 13, preferably a plug-in contact to be plugged into a conventional power supply jack in, for example, a wall.

The container 50 has a neck 54 with a neck insert or closure cap 51 which tightly holds a form stable, porous wick means 52, which is immersed in a liquid formulation 53, contained in the container 50. The upper part of the wick means 52 is surrounded by the heater unit 2 whereas the lower part of the wick 52 means reaches down to the bottom of the container 50.

The mounting 8 is formed on its inner periphery with a threaded portion 10 adapted for screw-thread engagement with a threaded portion 56 on the outer periphery of the neck 54 of the container 50. When the thermal vaporizer A is to be used, the container 50 is fixed into the mounting 8 by the screw-thread engagement of the threaded portions 10 and 56 whereby the wick means 52 of the container 50 is inserted into the heater unit 2 concentrically therewith.

Of course, alternatives to the screw-thread engagement between the threaded portions 10 and 56 for attaching the container 50 to the mounting 8 can be used and are well-known to any person skilled in the art. For example, the threaded portions 10 and 56 may be replaced by a projection and an indentation which are engageable with each other.

FIG. 2 shows a preferred embodiment of the mounting 8 for the container 50 with first selecting means 20 arranged above the mounting 8. FIG. 3 shows a preferred embodiment of the activating means 55 of the container 50 for activating the first selecting means 20 of the thermal vaporizer A, whereby said means comprise a protruding part 55 such as a molding on the neck 54 of the container.

The container 50 shown in FIG. 4a comprises activating means 55 in form of a protruding part, such as a molding, which is arranged to actuate the first selecting means 20 of the thermal vaporizer A by pressing and displacing said first selecting means 20 with the activating means 55 when the container 50 is fixed into the mounting 8 of the vaporizer A. The first selecting means 20 are actuated and thus not visible in FIG. 4a. After removing the container, the first selecting means 20 return to their original position. In a preferred embodiment this can be achieved by a spring fixed inside the first selecting means 20.

Figure 4B:
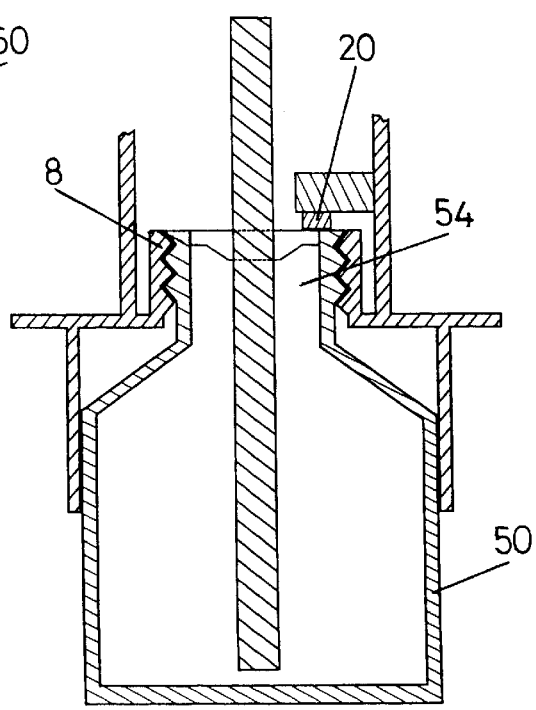

The sealing means or cap of the container 50 shown in FIG. 4b finishes with the neck 54 of the container 50. Therefore, the first selecting means 20 are not activated when this container is fixed into the mounting 8 of the vaporizer A.

Figure 5:
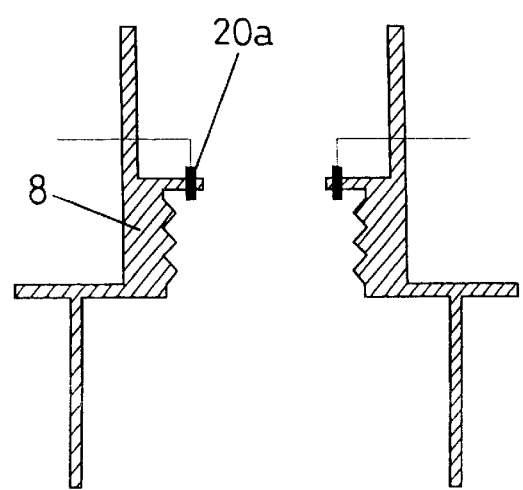
FIG. 5 shows a cross-sectional view of another preferred embodiment of the mounting.
Figure 6:
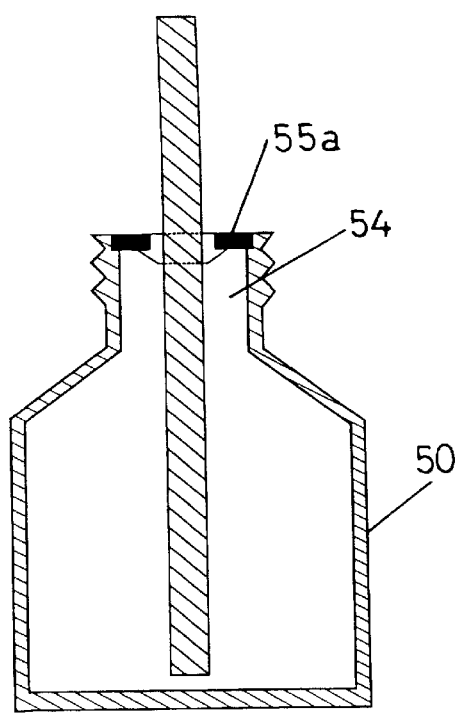
FIG. 6 shows a cross-sectional view of another preferred embodiment of the container.

The first selecting means 20a as shown in FIG. 5 comprise two electrical connections which are molded into the mounting 8 of the thermal vaporizer A. The activating means 55a shown in FIG. 6 which are arranged to activate the first selecting means 20a are electrical contacts comprising metal connectors on the neck 54 of the container 50.

Figure 7A:
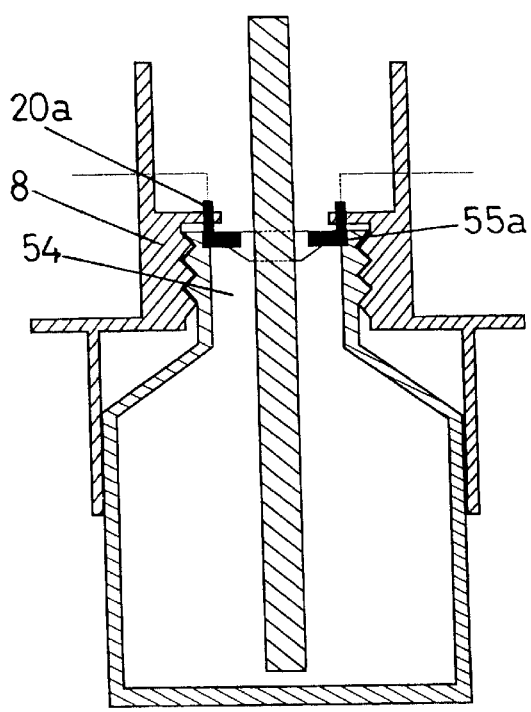
FIGS. 7a & 7b show cross-sectional views of the container within the mounting.

In FIG. 7a the same container 50 is fixed into the mounting 8 of the thermal vaporizer A. The activating means 55a on the neck 54 act on the first selecting means 20a of the thermal vaporizer.

Figure 7B:
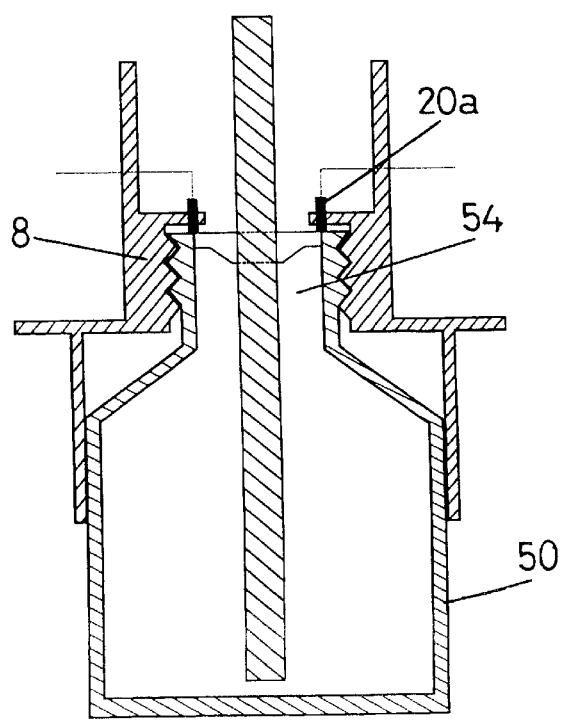

The sealing means of container 50 shown in FIG. 7b finish with the neck 54 of the container 50 and said container does not include any activating means. Therefore, the first selecting means 20a are not activated when the container 50 is fixed into the mounting 8 of the thermal vaporizer.

Figure 8A:
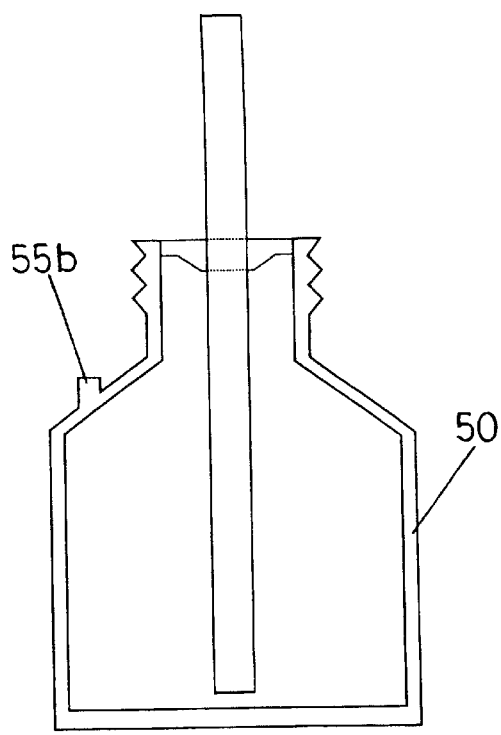
FIGS. 8a, 8b, 8c, 8d and 8e schematically illustrate some alternative embodiments of the container.

FIG. 8a illustrates a container in which the activating means 55b are embodied as a protruding part at the shoulder portion of the container, preferably embodied as a protrusion integrally molded with the container.

Figure 8B:
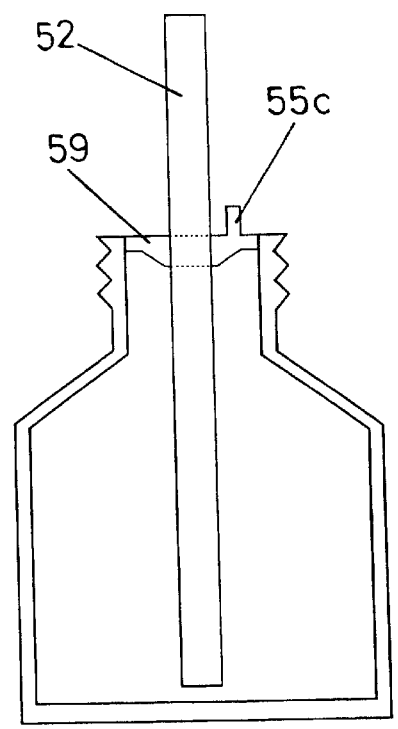

FIG. 8b illustrates a container in which the activating means 55c are embodied as a protruding part of a cap means 59 arranged at the mouth portion of the container and acting a means for holding the wick means 52.

Figure 8C:
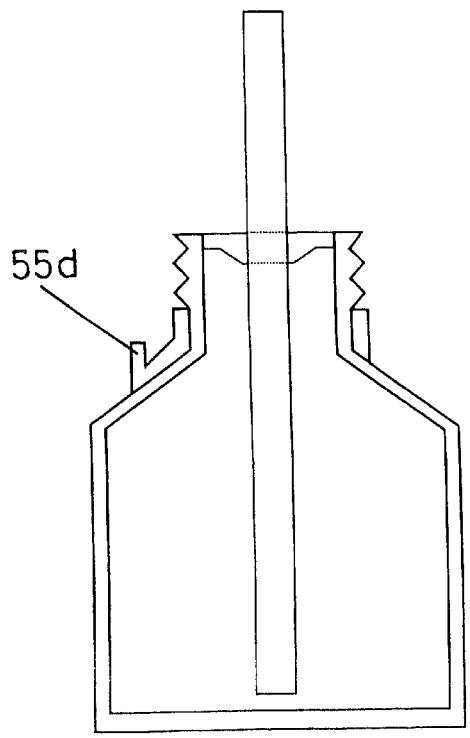

FIG. 8c illustrates an embodiment of the invention in which the activating means 55d are embodied as a protruding part arranged on a collar device attached to the container at its neck and/or shoulder portion.

Figure 8D:
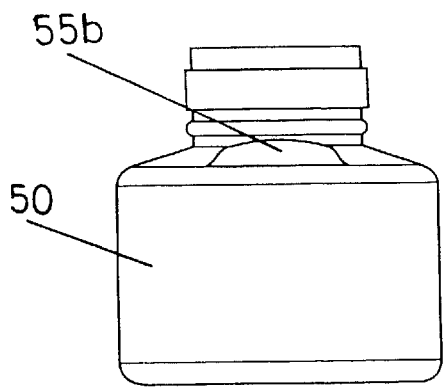
Figure 8E:
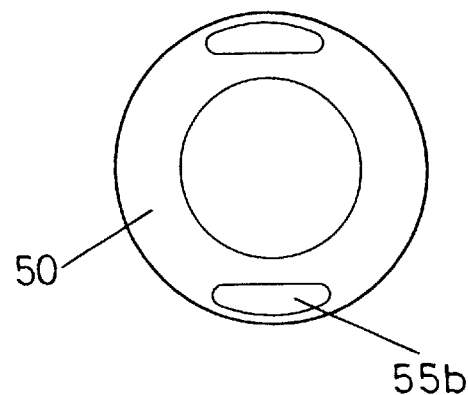

FIGS. 8d and 8e are a side view and top view, respectively, of a container in which the activating means 55b are embodied as two protruding parts with a slightly arcuate shape, substantially corresponding to segments of a circle around the longitudinal axis of the container (in this case, a bottle) and arranged at a shoulder portion of the bottle.

Figure 9:
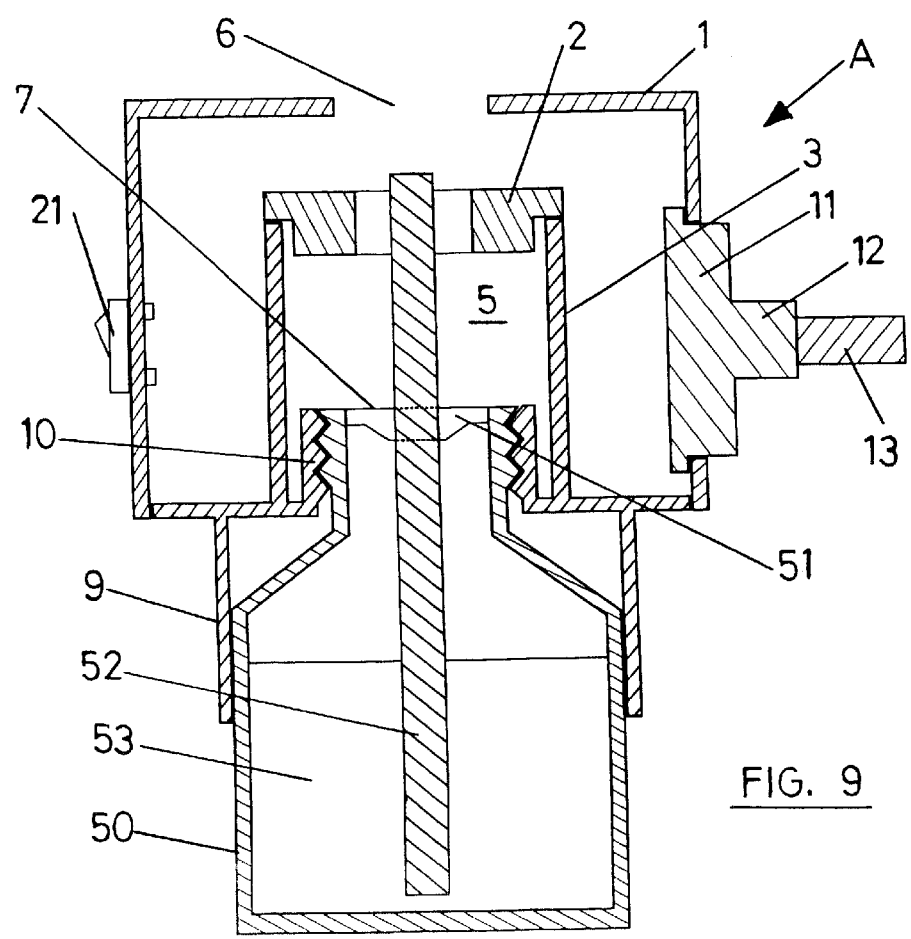
FIG. 9 shows a cross-sectional view of a thermal vaporizer as in FIG. 1, but with further second selecting means.

FIG. 9 illustrates a thermal vaporizer similar to the one illustrated in FIG. 1 but further provided with a second selecting means (21), comprising a rocker switch which can be switched between three different positions, as outlined above; with this switch, the vaporizer can be turned off ("off" operation mode) and on ("on" operation mode) and in the "on" operation mode, the user con choose between two different positions corresponding to different temperatures, for example, for low rate emission of fragrance and for high rate emission of fragrance (whereas, however, no insecticide emission should take place unless also the first selecting means are activated).

Figure 10A:
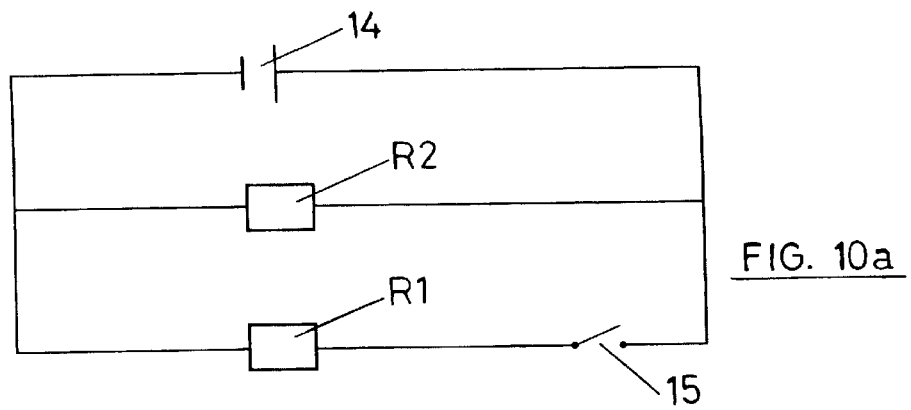
FIGS. 10a & 11b show schematic circuit diagrams corresponding to the electrical circuitry of the heater unit in accordance with a preferred embodiment of the invention.
Figure 10B:
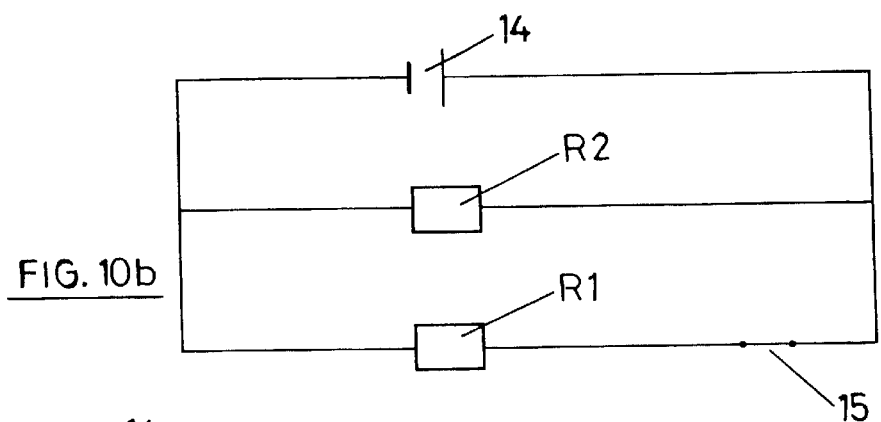

FIGS. 10a and 10b schematically illustrate the electric circuitry of the heater unit 2.

In FIG. 10a there is a primary circuit, in which a resistor R2 of the heater unit is connected to the supply voltage source 14. A secondary circuit comprises a resistor R1 and a switch 15 arranged to be closed by the first selecting means (20, 20a). If the switch 15 is open, the resistor R1 has no effect on the heater unit 2.

FIG. 10b shows the same circuit as illustrated in FIG. 10a, but in this case the switch 15 of the secondary circuit has been closed by the first selecting means (20, 20a), which has been actuated by the activating means 55 of the container 50, when said container 50 has been fixed into the mounting 8 of the thermal vaporizer A. In this case, the same voltage is applied over both resistors R2 and R1 which thus both are heated, whereby a higher temperature is obtained.

Figure 11A:
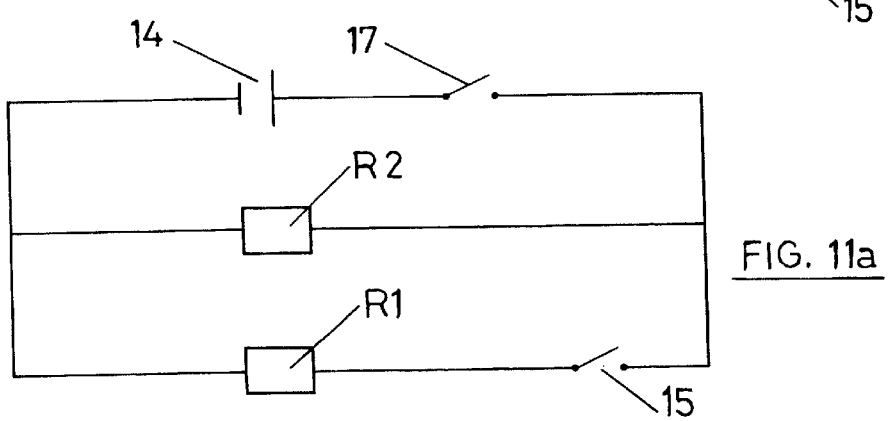
Figure 11B:
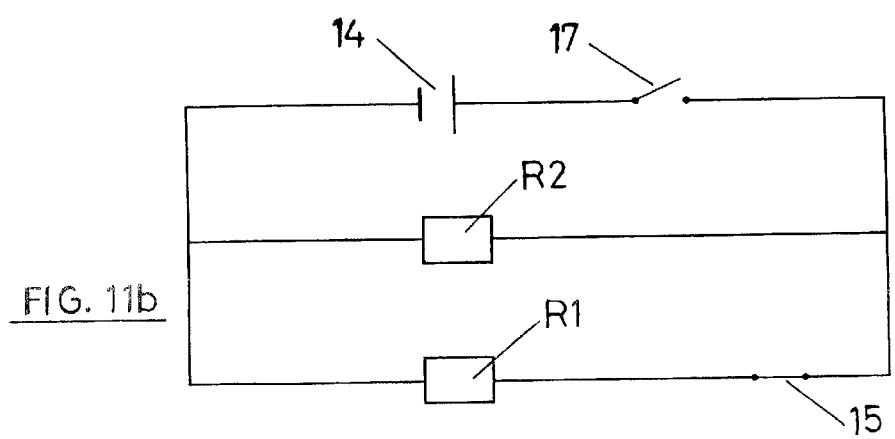

FIGS. 11a and 11b show another preferred lay-out of the circuitry. FIG. 11a shows a circuit similar to the one illustrated in FIG. 10a but with an additional "on-off" switch 17 which is closed when a container 50 is fixed into the mounting. Due to this switch the heater unit of thermal vaporizer A may only work, if a container is inserted. FIG. 11b shows the same circuit as the one of FIG. 11a but with a closed secondary circuit.

Figure 12:
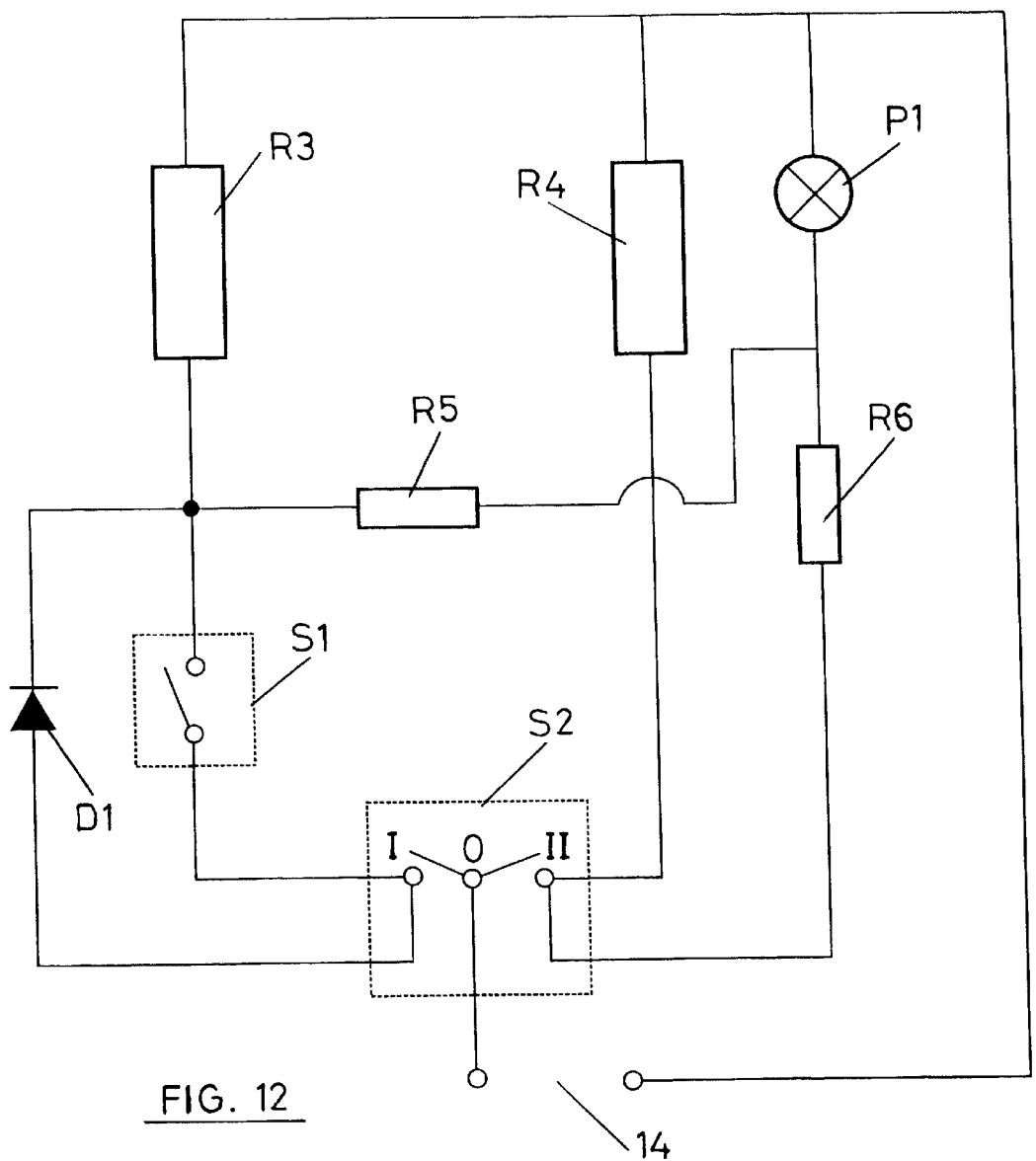
FIG. 12 shows a schematic circuit diagram corresponding to the electrical circuitry of the heater unit in accordance with another preferred embodiment of the invention.

FIG. 12 shows an alternative embodiment, in which a first branch comprises a switch S2, which is operatively associated with the first selecting means (20, 20a) and which is coupled in series with a first resistor R3 and in parallel with a diode D1. A second branch comprises a second resistor R4. A rocker switch S1 making up the second selecting means 21 as outlined above is arranged so as to apply one terminal of the supply voltage 14 source either to the first branch or to the second branch or to non of said branches. The resistors R3 and R4 make up the heating elements of the heating unit.

The circuit also includes some fuses (R5, R6) and a pilot lamp (P1).

If the rocker switch S1 is in the open position ("O"), the vaporizer is in the off operation mode, that is, no heating of the wick means will take place.

If the rocker switch is in the right-hand position ("II"), the supply voltage is applied over the resistor R4 which is thus heated. The resistance of said resistor is chosen so as to obtain a "medium" temperature.

If the rocker switch is in the left-hand position ("I"), the voltage is applied over the first resistor R3 and, if the switch S2 is open, also over the diode. In that case, and with a suitably chosen size of the resistor R3, a "low" temperature will be obtained in the heater unit.

With the same arrangement and with the rocker switch S1 in the left-hand position ("I"), if the first selecting means (20, 20a) are activated by the container, the switch S2 is closed and the entire supply voltage is applied over the resistor R3, thus giving rise to a "high" temperature in the heating unit, providing for emission of the insecticide.

Figure 13:
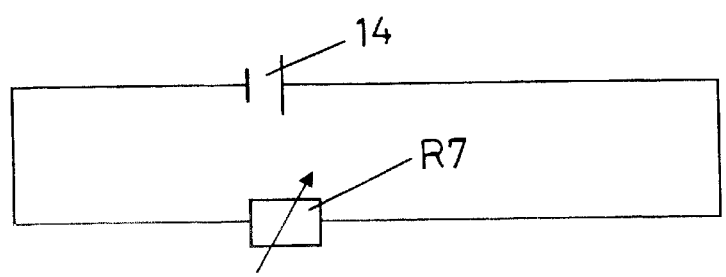
FIG. 13 shows a schematic circuit diagram corresponding to the electrical circuitry of the heater unit in accordance with another preferred embodiment of the invention.

In FIG. 13 an alternative embodiment of the heater unit is schematically shown; here, the means for selectively operating the heater unit comprise at least one variable resistor (R7), the effective resistance of which depends on a level of activation of the first selecting means.

Throughout the description and claims of the specification, the word "comprise" and variations of the word, such as "comprising", is not intended to exclude other additives, components, integers or steps.

What is claimed is:

1. A thermal vaporizer for a liquid formulation comprising a volatile active, said vaporizer (A) comprising a housing (1) having:
   a heater unit (2) for evaporating the liquid formulation;
   a mounting (8) for a container (50) for the liquid formulation;
   a passage (5) for a wick means (52) to be heated by the heater unit (2);
   at least one outlet (6) for evaporated volatile active;
   an electrical contact connected to said heater unit (2);
   characterized in that the vaporizer further comprises
      means for selectively operating the heater unit at, at least, two different predetermined heating temperatures, including selecting means for selecting heating temperature,
      said selecting means including at least one first selecting means (20, 20a) arranged to be selectively activated by the container (50).

2. A thermal vaporizer according to claim 1, wherein said first selecting means (20) is comprises a switch element arranged to be displaced by the container (50) when the container is fixed into the mounting (8).

3. A thermal vaporizer according to claim 1, wherein said first selecting means (20a) comprises at least one selectively interrupted electric circuit arranged to be closed by a metal connector on the container (50) when the container (50) is fixed into the mounting (8).

4. A thermal vaporizer according to claim 1, wherein the heater unit (2) has an annular shape enclosing the passage (5) for the wick means.

5. A thermal vaporizer according to claim 1, wherein the container (50) is arranged to be fixed into the mounting (8) by screw-thread engagement between an internally threaded portion of the mounting (8) and an externally threaded portion of the container (50).

6. A thermal vaporizer according to claim 1, wherein the selecting means further comprise, at least, a second selecting means (21) for selecting, at least, an off operation mode and an on operation mode.

7. A thermal vaporizer according to claim 6, wherein said second selecting means and said first selecting means are arranged so as to make the heater unit (20) operate at different temperatures, whereby the heater unit is arranged to operate at a specific high temperature only when the first selecting means (20, 20a) are activated by the container (50).

8. A thermal vaporizer according to claim 7, wherein the heater unit is arranged to operate at a low temperature when the second selecting means are in a first on operation mode position and the first selecting means are not activated by the container;

at a medium temperature when the second selecting means are in a second on operation mode position and the first selecting means are not activated by the container; and at a high temperature only when the first selecting means are activated by the container.

9. A thermal vaporizer according to claim 1, wherein the means for selectively operating the hater unit include, at least, a first branch comprising a first resistor (R3) and, in series with said resistor, a circuit comprising a diode (D1) and a switch (S2) coupled in parallel, so that when said switch (S2) is in an open position, a supply voltage is applied over the diode and over the first resistor, and when the switch (S2) is in a closed position, the supply voltage is applied over the first resistor and not over the diode, the switch (S2) being arranged to be in the open position when the first selecting means (20, 20a) are not activated by the container and in the closed position when the first selecting means (20, 20a) are activated by the container.

10. A thermal vaporizer according to claim 9, wherein the means for selectively operating the heater unit further comprise a second branch comprising a second resistor (R4), said second branch being arranged in parallel with said first branch, whereby second selecting means (21) are arranged so that depending on the position of said second selecting means, voltage is applied selectively to the first branch or to the second branch so that heating is selectively performed by said first (R3) or by said second (R4) resistor.

11. A thermal vaporizer according to claim 1, wherein the means for selectively operating the heater unit comprise at least one variable resistor (R7) the effective resistance of which depends on a level of activation of the first selecting means.

12. A thermal vaporizer according to claim 1 for a fragrance and/or a insecticide.

13. A thermal vaporizer according to claim 8, wherein the high temperature corresponds to a temperature for vaporizing an insecticide and wherein the low temperature corresponds to a temperature for low rate release of a fragrance and wherein the medium temperature corresponds to a temperature for high rate release of a fragrance.

14. A container (50) for the thermal vaporizer (A) according to claim 1, characterized in that the container is provided with activating means (55, 55a, 55b, 55c, 55d) for activating the first selecting means (20) of the thermal vaporizer when the container (50) is fixed into the mounting(8).

15. A container according to claim 14, wherein the activating means comprises a protruding part (55, 55b, 55c, 55d) of the container.

16. A container according to claim 15, wherein the protruding part is a molding.

17. A container according to claim 15, wherein the protruding part (55, 55c) is arranged at a mouth portion of the container (50).

18. A container according to claim 15, wherein the protruding part (55b, 55d) is arranged at a neck or shoulder portion of the container (50).

19. A container according to claim 15, wherein the protruding part (55, 55b, 55c, 55d) is a part forming an integral part of the container (50).

20. A container according to claim 15, wherein the protruding part (50, 55b, 55c, 55d) is a part of an independent element arranged to be attached to the container (50).

21. A container according to claim 14, wherein the activating means comprise a metal connector (55a).

* * * * *